United States Patent
Wang (10) Patent No.: US 9,360,479 B2
(45) Date of Patent: Jun. 7, 2016

(54) RAPID LATERAL FLOW ASSAY METHOD FOR LOW QUANTITY LIQUID OR DRY SAMPLES

(71) Applicant: Daniel Wang, San Diego, CA (US)

(72) Inventor: Daniel Wang, San Diego, CA (US)

( * ) Notice: Subject to any disclaimer, the term of this patent is extended or adjusted under 35 U.S.C. 154(b) by 0 days.

(21) Appl. No.: 15/000,999

(22) Filed: Jan. 19, 2016

(65) Prior Publication Data

US 2016/0131645 A1    May 12, 2016

Related U.S. Application Data

(63) Continuation-in-part of application No. 14/606,908, filed on Jan. 27, 2015, which is a continuation-in-part of application No. 14/258,968, filed on Apr. 22, 2014, now abandoned, which is a continuation-in-part of application No. 13/678,140, filed on Nov. 15, 2012, now abandoned.

(51) Int. Cl.
*G01N 21/75* (2006.01)
*G01N 33/558* (2006.01)
(Continued)

(52) U.S. Cl.
CPC ............ *G01N 33/558* (2013.01); *B01L 3/5023* (2013.01); *B01L 3/5027* (2013.01); *B01L 3/00* (2013.01); *B01L 3/508* (2013.01);
(Continued)

(58) Field of Classification Search
CPC . G01N 33/558; G01N 33/53; G01N 33/5302; G01N 21/8483; G01N 21/78; G01N 2035/00108; B01L 2300/0825; B01L 3/5023; B01L 3/502715; B01L 2400/0406; B01L 3/50273; B01L 2200/027; B01L 3/502746; B01L 2200/025; B01L 2200/026; B01L 2200/12; B01L 2200/16; B01L 2300/025; B01L 2300/06; B01L 2300/041; B01L 2300/047; B01L 2300/0609; B01L 2300/069
See application file for complete search history.

(56) References Cited

U.S. PATENT DOCUMENTS

| | | |
|---|---|---|
| 4,855,240 A | 8/1989 | Rosenstein et al. |
| 5,120,643 A | 6/1992 | Ching et al. |

(Continued)

FOREIGN PATENT DOCUMENTS

WO    WO/99/06827 A2    2/1999

OTHER PUBLICATIONS

Posthuma-Trumpie GA, Korf J, Van Amerongen A. Lateral flow (immuno)assay: its strengths, weaknesses, opportunities and threats. A literature survery. Anal Bioanal Chem. Jan. 2009. 393(2): 569-582. Groningen, The Netherlands.

(Continued)

*Primary Examiner* — Dennis M White (57) ABSTRACT

This invention describes a device for assaying a dry or small volume liquid sample on a lateral flow capillary assay by utilizing a supplementary non-sample aqueous solution that will push the sample up the assay without diluting or significantly diluting the original sample. This invention enables a sample to be assayed rapidly and/or on-site when the sample is in dried or solid form, or when the liquid volume is too small to complete an assay. As an option, the device can display a colored signal when a sufficient amount of liquid sample has been collected or added to the device. The minimal liquid volume requirement of the device significantly reduces the sample collection time to a matter of seconds and resolves situations in which fluids available for collection are not abundant. Therefore, this invention allows the lateral flow test device to be a more rapid, efficient, and versatile apparatus.

9 Claims, 8 Drawing Sheets

(51) Int. Cl.
*B01L 3/00* (2006.01)
*G01N 35/00* (2006.01)
*G01N 21/84* (2006.01)
*G01N 21/78* (2006.01)
*G01N 33/53* (2006.01)
*B01L 9/00* (2006.01)

(52) U.S. Cl.
CPC ....... *B01L 3/50273* (2013.01); *B01L 3/502715* (2013.01); *B01L 3/502723* (2013.01); *B01L 3/502738* (2013.01); *B01L 3/502746* (2013.01); *B01L 9/52* (2013.01); *B01L 2200/025* (2013.01); *B01L 2200/026* (2013.01); *B01L 2200/027* (2013.01); *B01L 2200/0689* (2013.01); *B01L 2200/12* (2013.01); *B01L 2200/16* (2013.01); *B01L 2300/025* (2013.01); *B01L 2300/041* (2013.01); *B01L 2300/047* (2013.01); *B01L 2300/069* (2013.01); *B01L 2300/0609* (2013.01); *B01L 2300/0636* (2013.01); *B01L 2300/0645* (2013.01); *B01L 2300/0654* (2013.01); *B01L 2300/087* (2013.01); *B01L 2300/089* (2013.01); *B01L 2300/0819* (2013.01); *B01L 2300/0825* (2013.01); *B01L 2400/0406* (2013.01); *B01L 2400/0475* (2013.01); *B01L 2400/0633* (2013.01); *B01L 2400/086* (2013.01); *G01N 21/78* (2013.01); *G01N 21/8483* (2013.01); *G01N 33/53* (2013.01); *G01N 33/5302* (2013.01); *G01N 2035/00108* (2013.01)

(56) References Cited

U.S. PATENT DOCUMENTS

| | | |
|---|---|---|
| 5,569,608 A | 10/1996 | Sommer |
| 5,591,645 A | 1/1997 | Rosenstein |
| 5,656,503 A | 8/1997 | May et al. |
| 5,905,029 A | 5/1999 | Andreotti et al. |
| 6,303,081 B1 | 10/2001 | Mink et al. |
| 7,192,555 B2 | 3/2007 | Mink et al. |
| 2007/0286771 A1 | 12/2007 | Nunes et al. |

OTHER PUBLICATIONS

Kaufman E, Lamster I. The diagnostic applications of saliva—A review. Crit Rev Oral Biol Med. Mar. 2002. 13(2): 2197-212. New York, New York, USA.

Mittal S, Bansal V, Garg S, Atreja G, Bansal S. The diagnostic role of saliva—A review. J Clin Exp Dent. 2011. 3(4): e314-20. Haryana, India.

Bogdanovic J, Koets M, Sander I, Wouters I, Meijster T, Heederik D, Van Amerongen A, Doekes G. Rapid detection of fungal α-amylase in the work environment with a lateral flow immunoassay. Nov. 2006. 118(5): 1157-1163. Wageningen and Zeist, The Netherlands, and Bochum, Germany.

Tsay A, Williams L, Mitchell EB, Chapman MD. A rapid test for detection of mite allergens in homes. Clin Exp Allergy. Nov. 2002. 32(11): 1596-1601. Charlottesville, Virginia, USA.

Carter DJ, Cary RB. Lateral flow microarrays: a novel platform for rapid nucleic acid detection based on miniaturized lateral flow chromatography. Nucl Acids Res. May 2007. 35(10): e74. Los Alamos, New Mexico, USA.

Drummer O. Drug testing in oral fluid. Clin Biochem Rev. Aug. 2006. 27(3): 147-159. Southbank, Victoria, Australia.

Schramm W, Craig PA, Smith R, Berger G. Cocaine and benzoylecgonine in saliva, serum, and urine. Clin Chem. Mar. 1993. 39(3): 481-487. Ann Arbor, Missouri, USA.

Shrivastava S, Bastian TS, Singh A, Jaiswal R. The use of saliva as an unconventional sample for drug detection: A review. Medico-Legal Update. 2008. 8(2). Lucknow, India.

RAPID LATERAL FLOW ASSAY METHOD FOR LOW QUANTITY LIQUID OR DRY SAMPLES

CROSS-REFERENCE TO RELATED APPLICATIONS

This application is a continuation-in-part of application Ser. No. 14/606,908, filed 27 Jan. 2015, which is a continuation-in-part of application Ser. No. 14/258,968, filed 22 Apr. 2014, which is a continuation-in-part of application Ser. No. 13/678,140, filed 15 Nov. 2012.

FIELD OF THE INVENTION

This invention relates to a method and system for detecting one or more target analytes in small volume liquid or dry samples, such as bodily fluids, or those obtained from the surface of objects or the environment. The device design requires the testing of a sample with a supplemental non-sample aqueous solution that allows a small volume liquid or dry sample to be assayed.

BACKGROUND OF THE INVENTION

Within the last few decades, numerous rapid lateral flow assays have been developed and implemented for determining the presence or absence of specific analytes in bodily fluids, such as in blood, urine, saliva; on the surface of objects in the environment; and in other dried and aqueous substances. Multiple patents have been awarded for the development of such lateral flow assay techniques (U.S. Pat. Nos. 4,855,240, 5,120,643, 5,569,608, 5,591,645, 5,656,503, 6,303,081, 7,192,555, and WO/1999/006827). Rapid lateral flow assays are commonly used to detect diseases, drugs, hormones, bacteria, viruses, and biomarkers in human bodily fluids (1-3). Published scientific literature has demonstrated the wide application of lateral flow assays to screen human urine, saliva, and/or blood/serum/plasma for testing or monitoring:

- Autoimmune disorders, such as Sjögren's syndrome (SS)
- Cancers, such as ovarian cancer, breast cancer, prostate cancer, and oral squamous cell carcinoma
- Cardiovascular diseases, such as atherosclerosis
- Diabetes
- Drugs, including anti-epileptic drugs; psychiatric medicines; and illicit drugs such as lithium, carbamazepine, cotinine, amphetamines, barbiturates, cannabinoids, cocaine, diazepines, ethanol, opioids, and phencyclidine
- Hereditary diseases, such as 21-Hydroxylase deficiency
- Hormone levels, such as for aldosterone, cortisol, dehydroepiandrosterone, estradiol, estriol, human chorionic gonadotropin (hcG), progesterone, and testosterone
- Infectious diseases, such as brucellosis, *Chlamydia*, *Helicobacter pylori* infection, Leptospirosis, Lyme disease, neurocysticerosis, pigeon breeder's disease (PBD), schistosomiasis, and shigellosis
- Oral health, such as oral candidiasis, oral bacteria monitoring, and periodontal disease
- Psychiatric therapy, such as monitoring therapeutic responses to the treatment of anxiety and measuring post-traumatic stress disorder (PTSD)
- Renal disease
- Vaccination confirmation, such as for anthrax
- Viral diseases, such as cytomegalovirus (CMV); dengue; Epstein-Barr virus (EBV); hepatitis A, B, and C; human herpes virus 6, 7, and 8; human immunodeficiency virus (HIV); human rabies; measles; mumps; rotavirus (RV); and rubella Rapid lateral flow assay devices also have established applications for food contaminant and environmental pollutant testing. Published scientific literature has demonstrated the use of lateral flow assays for detecting antibiotics, pesticides, bacteria, and viruses in food products such as fruits, plants, vegetables, grains, milk, eggs, meat, and animal feed. In addition, various published scientific literatures have demonstrated the application of rapid lateral flow assays for testing substances on the surfaces of objects (4-6, U.S. Patent Application No. 20070286771). Recent developments include allergen detection such as fungal a-amylase, a flour allergen commonly responsible for asthma, and mite allergens; and the detection of biothreat agents such as *Baccilis anthracis*, the etiologic agent of anthrax, and explosive residue, on contaminated surfaces. Food preparation and medical facilities have also implemented the use of rapid lateral flow assays that screen surfaces for Adenosine triphosphate (ATP) to examine if such surfaces are clean and free from microorganisms (U.S. Pat. No. 5,905,029).

Though many different applications have been demonstrated, drugs of abuse (DOA) testing is one of the most universal implementations for the rapid lateral flow assay. DOA testing is currently a multi-billion-dollar industry exhibiting significant market growth due to the increase in illicit drug use, the emergence of new drugs, and the rise in awareness of societal and personal consequences associated with illicit drug use. Main consumers consist of medical clinics; law enforcement; and employers that perform pre-employment screening, random employee testing, and/or government-mandated DOA testing. DOA testing consists of assays that test human urine, saliva, and blood for illicit substances. Although oral fluid testing has obvious advantages over urine and blood testing, the DOA testing market is dominated by the use of rapid lateral flow assays that test urine samples. The primary benefit of oral testing is its ability to negate privacy concerns. Saliva testing is comparable to conducting an oral temperature reading with a thermometer in that sample collection is performed face-to-face, leaving little to no chance of sample adulteration by the drug user. Oral fluid testing can also detect parent tetrahydrocannabinol (THC) in saliva, which is of great significance since parent THC presence indicates present drug influence. Other benefits include user-friendliness, convenience for on-site testing, non-invasiveness, and the ability to repeat sampling. Equally important is the close correlation of drug concentrations in oral fluid to that in blood (2, 7, 8).

Saliva is a unique bodily fluid and its popularity as a diagnostic medium has advanced exponentially in the last 10 years. In the United States, the need for further research in salivary diagnostics has been emphasized by federal action plans emanating from the Office of the Surgeon General [Health and Human Services (HHS), 2009] and the National Institute of Dental and Craniofacial Research (NIDCR, 2009). The literature is replete with over 2,500 articles since 1982, describing the use of saliva, gingival crevicular fluid, and mucosal transudates for drug monitoring and for the detection of various oral and systemic maladies.

While oral fluid rapid DOA testing has obvious merits, technical obstacles that limit its broad applications still exist today. For instance, the duration of sample collection with currently available collection devices can be too time-consuming due to the variable nature of saliva attributable to viscosity, mouth dryness, age, gender, and time of saliva collection (9). Collecting a sufficient volume of oral fluid for conducting a test run may take more than 5 minutes, yet in many cases collecting a sufficient sample volume can be unfeasible. Indeed, the necessary volume for a sample to mix and bind to its ligand in a lateral flow assay is often as little as less than 0.05 milliliters; however, this volume is not sufficient to maintain the capillary flow required to complete the test run.

Assaying a sample with an insufficient volume on a conventional lateral flow device can produce invalid results as the sample will not have the ability to run to completion. When a sufficient volume of a sample is unattainable or a only a small volume of a sample of interest remains, a test administrator may opt to dilute the sample in order to meet the larger sample volume requirements of a conventional lateral flow device. Nevertheless, screening a diluted sample can cause inaccurate test results as the concentration of the target analyte(s) may have been significantly diluted to an undetectable range. This can increase the chance of obtaining a false negative result, which can have serious ramifications for any type of screening. Conventional rapid lateral flow devices that test dry or solid samples, such as those from object surfaces, usually contain a reagent or solution that is directly added to the sample or preloaded onto the sample collecting component so that the dry or solid substance will be diluted in the solution.

With the growth of advanced applications for rapid lateral flow assays, it is clear that there is an unmet need for a rapid lateral flow device that is capable of testing small volume liquid samples as well as dry or solid samples while maintaining sample integrity.

BRIEF SUMMARY OF THE INVENTION

This invention pertains to a device for assaying a small volume liquid or dry sample on a rapid, lateral flow capillary assay. For dry or solid samples, the device allows a sample to be assayed rapidly and on-site by utilizing a supplementary non-sample aqueous solution that acts as a solvent to push the sample up the assay. For liquid samples, the device minimizes the volume of a sample required to run an assay by utilizing the supplementary non-sample aqueous solution to aid the flow of a small volume liquid sample. For both dry and liquid samples, the device is capable of employing the supplementary non-sample aqueous solution without diluting or only minimally diluting the original sample so that a lengthy, large volume sample collection method becomes unnecessary and a liquid sample can be assayed even if only a small volume of fluid is available for collection. The minimal liquid volume requirement of the device significantly reduces the sample collection time to a matter of seconds and resolves situations in which fluids available for collection are not abundant, therefore making the lateral flow test device a much faster and more efficient apparatus.

As an option, the device can contain a sample sufficiency window that will display a colored marker when the sample volume is sufficient to run the assay. The sample sufficiency marker functions as a colored signal so that test administrators can easily determine when a sufficient amount of sample has been collected, and/or if a certain volume of liquid is sufficient for running the assay. The sample sufficiency marker is intended to serve as a simple indication of sample collection completion for liquid samples and is particularly useful for small volume or trace amount samples.

The device consists of an analyte testing unit and an auxiliary cap, which has a liquid-holding chamber containing a flexible, sponge or fibrous material preloaded with a non-sample aqueous solution. The analyte testing unit is composed of a single unit that integrates the sample testing component(s) with a sample collecting component, which is made up of an absorbent material. The analyte testing unit is housed by a cassette that protects and secures the position of the sample collecting component and the sample testing component(s). The sample collecting component slightly overlaps with the sample receiving area(s) of the sample testing component(s) so that the sample continuously migrates up the assay under capillary action. The sample collecting component can also contain a colored marker that will migrate up its absorbent material when a sufficient volume of liquid sample has been added. For dry samples, the colored marker will not indicate sample sufficiency. The sample collecting component is placed into the liquid-holding chamber of the auxiliary cap after a sufficient amount of sample has been added or collected, wherein the sample collecting component will come into contact with the sponge or fibrous material preloaded with a non-sample aqueous solution, allowing a dry or small volume liquid sample to successfully run across the assay. The sample collecting component and sponge or fibrous material within the liquid-holding chamber of the auxiliary cap are positioned and designed so that such components come into minimal contact, allowing the sample to reach the binding or reaction area of the sample testing component as an undiluted or minimally diluted sample. For dry samples, the front portion of the supplemental non-sample aqueous solution will dissolve the dry substance, causing the front flow to contain the heist concentration of the sample that will run through the binding area of the solid support first. For liquid samples, the supplemental non-sample aqueous solution will push the sample by the capillary force so that the sample can run through the assay first, followed by the supplemental non-sample aqueous solution. The invention allows rapid testing to be performed with dry or solid samples, and low quantity liquid samples without significantly dilution; and with a visual marker for liquid sample sufficiency; thereby increasing the speed of sample collection and rapid analyte testing versatility, while decreasing the chances of unsuccessful assay runs due to a lack of sample abundance or insufficient sample volumes.

DETAILED DESCRIPTION OF THE INVENTION

Methods, systems, techniques and materials pertaining to an embodiment of the invention for performing a lateral flow capillary assay with a dry or solid, and small volume liquid sample are described.

Figure 1:
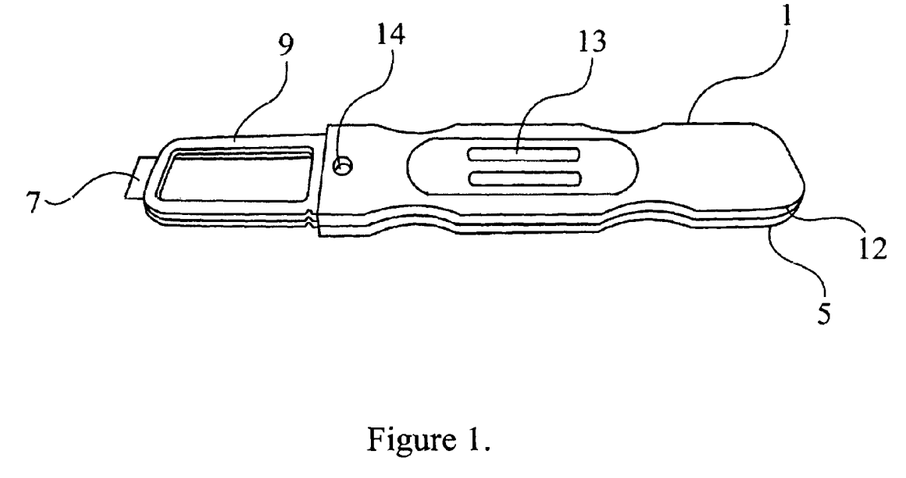
FIG. 1 is a perspective view of an analyte testing unit composed of two sample testing components.
Figure 2:
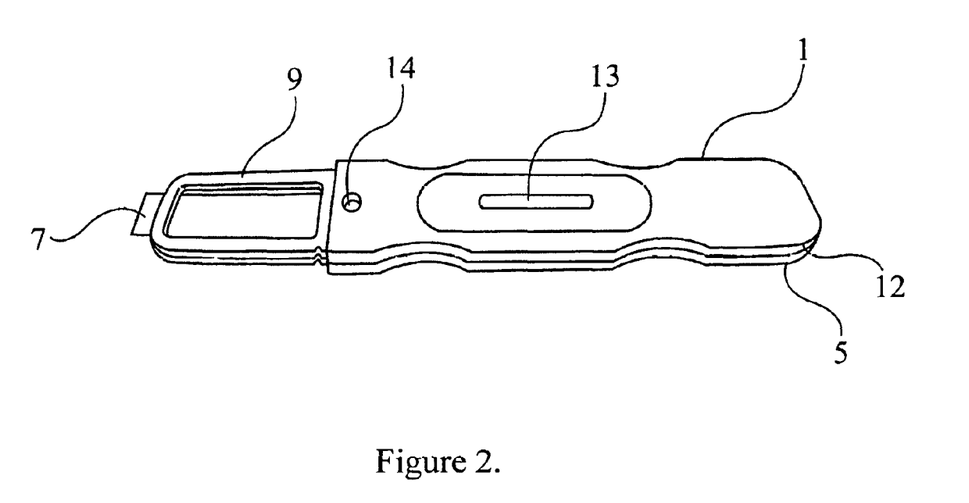
FIG. 2 is a perspective view of an analyte testing unit composed of one sample testing component.
Figure 3:
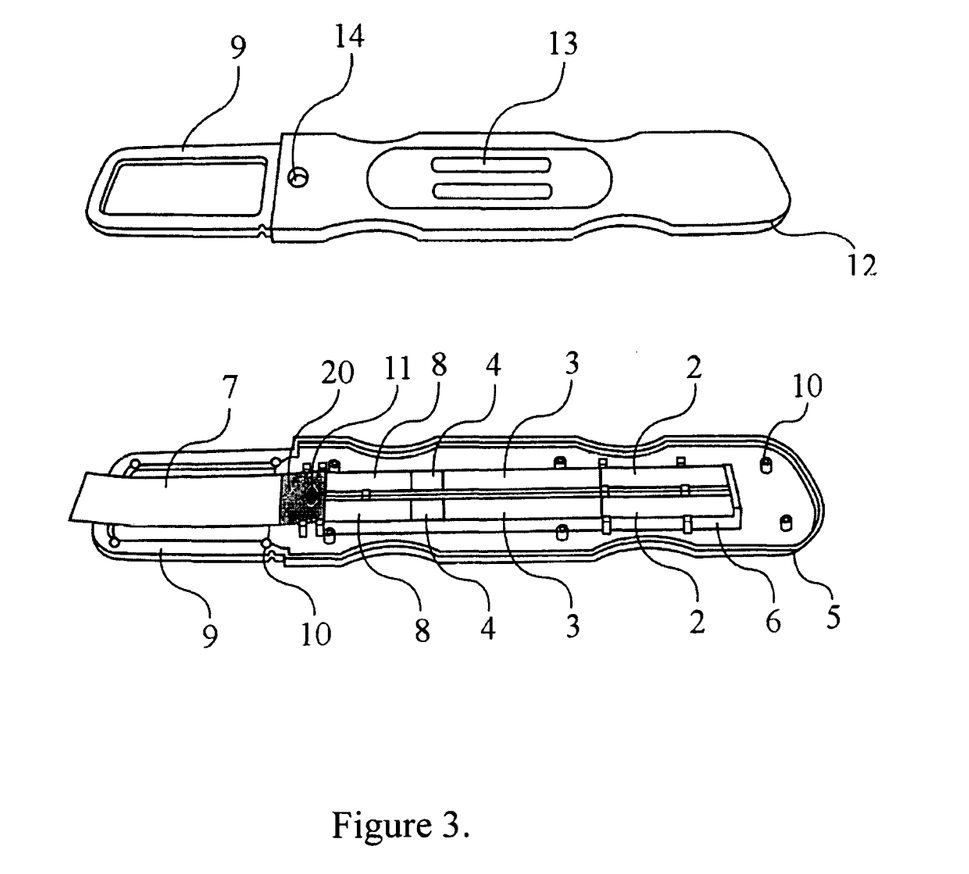
FIG. 3 is a perspective view of the inner structure of an analyte testing unit composed of two sample testing components.

With reference to FIGS. 1-8, the device for performing a lateral capillary flow assay comprises an analyte testing unit 1 and a corresponding auxiliary cap 15. FIG. 1 depicts an analyte testing unit 1 composed of two sample testing components or test strips. The top cassette 12 of the housing component consists of two test strip windows 13 that display the solid support 3 for reading assay results, and a sample sufficiency window 14 that displays a small, circular portion of the sample collecting component 7. The sample collecting component 7 consists of an absorbent material that collects or absorbs a sample and its length can extend slightly beyond the sample collecting tip 9 of the housing component as shown in FIG. 1-3, or fit exactly within the confines of the sample collecting tip 9, but must not be longer than the length of the auxiliary cap 15 chambers.

FIG. 3 shows the inner structure of an analyte testing unit 1 composed of two sample testing components or test strips. The bottom cassette 5 of the housing component contains an inner sub-shell structure 6 that surrounds each sample testing component or test strip so that these components are securely contained and remain in a fixed position. The sample collecting component 7 contains a colored marker 11, which is temporarily held in an unexposed area of the housing cassette below the sample sufficiency window 14. The colored marker 11 visually indicates sample sufficiency in the sample sufficiency window 14 when a sufficient volume of a liquid sample has been added to or collected by the sample collecting component 7. This sample sufficiency marker 11 is composed of a visually identifiable color or dye material. The sample collecting component 7 also contains a protective material 20 over its top edge, to ensure that the colored marker 11 does not migrate upwards onto the sample testing component or test strip. This protective material covers the top of the sample collecting component 7 without blocking the contact between the sample collecting component 7 and the sample receiving areas 8 of the test strips. The sample collecting tip 9 of the housing component exposes the sample collecting portion of the sample collecting component 7 while securely containing and fixing the position of the sample collecting component 7. The sample collecting component 7 must slightly overlap both sample receiving areas 8 of each test strip so that the sample can successfully flow from the sample collecting component 7 to the sample receiving areas 8.

As shown in FIG. 3, each sample testing component or test strip consists of a sample receiving area 8, an indicator holding area 4, a solid support 3, and a sample ending area 2. The sample receiving area 8 of the test strip is composed of an absorbent material to receive the sample from the sample collecting component 7. The indicator holding area 4 of the test strip temporarily holds at least one type of indicator material that binds with a corresponding target analyte in the sample to form an analyte-indicator complex that flows across the test strip under capillary action. The solid support 3 of the test strip contains at least one binding area to immobilize at least one type of binder material configured to bind with the at least one type of indicator material, at least one analyte, or both the at least one analyte and at least one type of indicator material, wherein a presence of the corresponding type of indicator material at the at least one binding area indicates an absence of a corresponding type of target analyte; and a separate validation area comprising a ligand or a binder material that selectively binds to the at least one type of indicator material to confirm that the at least one type of indicator material properly flowed across the test strip under capillary action. The sample ending area 2 of the test strip consists of an absorbent material that will receive the remaining sample and indicator materials that have migrated through the solid support 3. The binding area and the validation area of the solid support 3 are exposed by the test strip windows 13 of the top cassette 12 of the housing component for reading assay results. The top cassette 12 attaches to the bottom cassette 5 of the housing component via 10 corresponding nodules 10 surrounding the inside of both cassette parts to further affix the position of and protect the sample collecting component 7 and the sample testing components or test strips.

Figure 8:
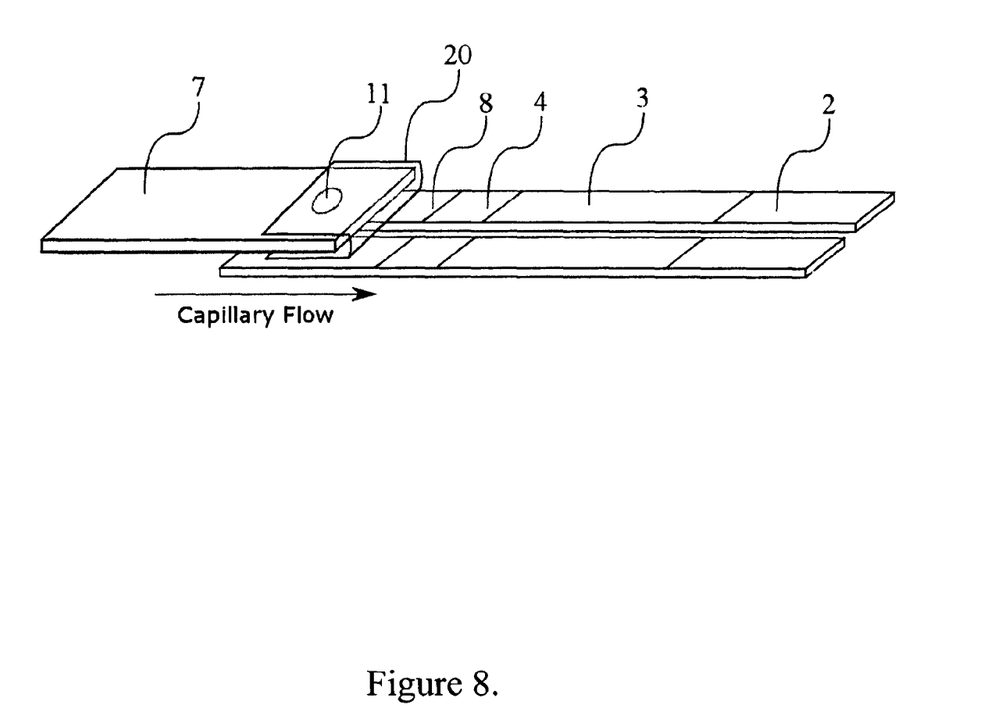
FIG. 8 is a perspective view of the sample collecting component overlapping two sample testing components, with the direction of capillary flow indicated.

As shown in FIG. 8, the sample collecting component 7 overlaps the sample receiving areas 8 of the sample testing components. The protective covering 20 wraps the top edge of sample collecting component 7 and covers the sample sufficiency marker 11. As the sample sufficiency marker 11 and the sample flows downstream towards the top edge of 7, the protective covering 20 prohibits movement of 11 from 7 onto The protective covering 20 does not cover the entirety of the overlap between sample collecting component 7 and sample receiving areas 8, allowing for direct contact between 7 and 8. The sample is therefore able to directly transfer from sample collecting component 7 and sample receiving areas 8, without being inhibited by protective covering 20.

FIG. 2 depicts an analyte testing unit 1 is composed of only one sample testing component or test strip; the top cassette 12 of the housing component is composed of only one test strip window 13; and the bottom cassette 5 of the housing component is composed of one inner sub-shell structure 6 surrounding the single sample testing component or test strip.

Figure 4:
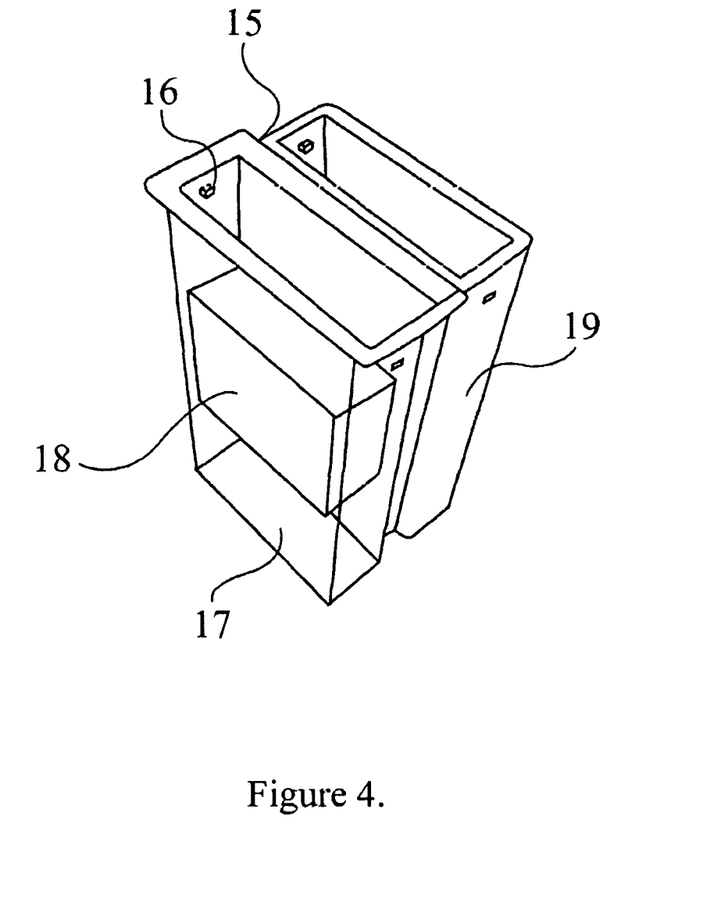
FIG. 4 is a perspective, transparent view of an auxiliary cap with two chambers.
Figure 6:
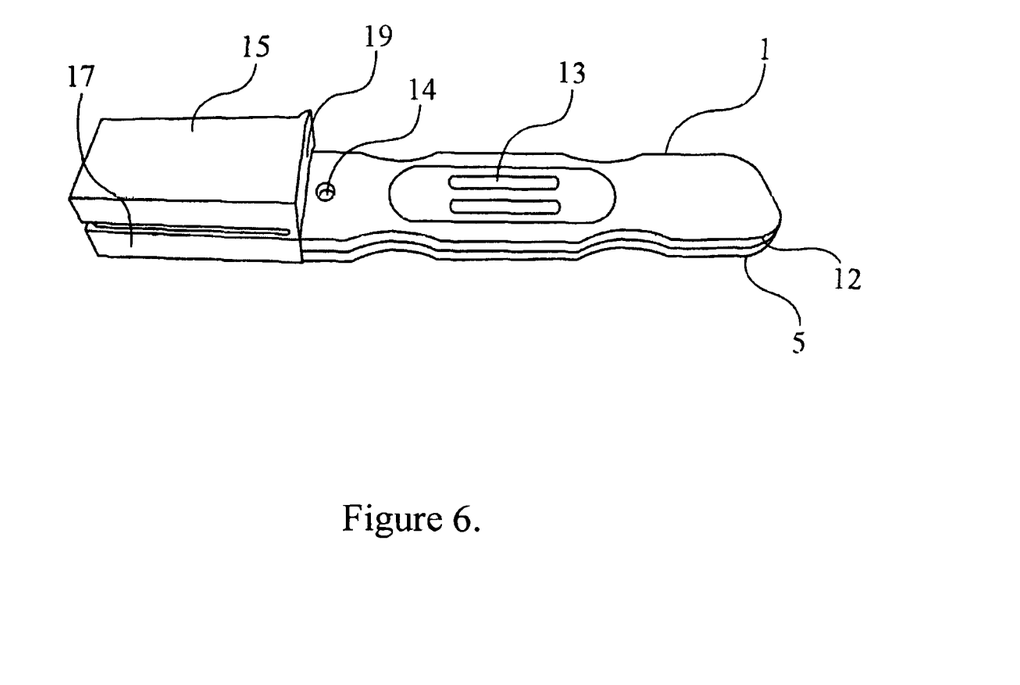
FIG. 6 is a perspective view of an analyte testing unit composed of two sample testing components placed into the liquid-holding chamber of a dual chamber auxiliary cap.

FIG. 4 shows a transparent view of a dual chamber auxiliary cap 15 consisting of a liquid-holding chamber 17 that contains the sponge or fibrous material 18, which is preloaded with a non-sample aqueous solution, and an empty chamber 19. The non-sample aqueous solution within the sponge or fibrous material 18 will aid the small volume liquid or dry sample to flow up the assay to complete a test run with a minimal volume requirement. This non-sample aqueous solution can consist of water, a mixture of organic and inorganic solutions at variable ratios with the inorganic solution content preferably above 50%, or chemical buffers with a pH range from 3 to 10 and a mole concentration between 0 to 2 moles. The empty chamber 19 of the dual chamber auxiliary cap 15 can be used to protect the sample collecting component 7 prior to sample collection. Each chamber contains two nodules 16, located on inner chamber walls near the opening of the cap, that will secure the sample collecting tip 9 into the chamber by interlocking with corresponding grooves on the sample collecting tip 9 of the housing cassette. When the sample collecting tip 9 is inserted into the liquid-holding chamber 17 of the auxiliary cap, the sample collecting component 7 will come into contact with the non-sample aqueous solution within the sponge or fibrous material 18. FIG. 6 depicts the sample collecting tip 9 of the housing cassette locked into the liquid-holding chamber 17 of the dual chamber auxiliary cap 15. The sponge or fibrous material 18 in the liquid-holding chamber 17 of the auxiliary cap 15 and the sample collecting component 7 are positioned and designed so that they only minimally contact when the sample collecting component 7 is placed into the auxiliary cap 15. This allows the sample to migrate to the sample receiving area 8 as an undiluted or minimally diluted sample. The volume of non-sample aqueous solution ranges from 0.05 milliliters to 2 milliliters, depending on the number of test strips in the analyte testing unit 1. The opening of the liquid holding chamber 17 of the auxiliary cap 15 will be sealed prior to analyte testing to ensure that the non-sample aqueous solution preloaded into the sponge or fibrous material does not evaporate.

Figure 5:
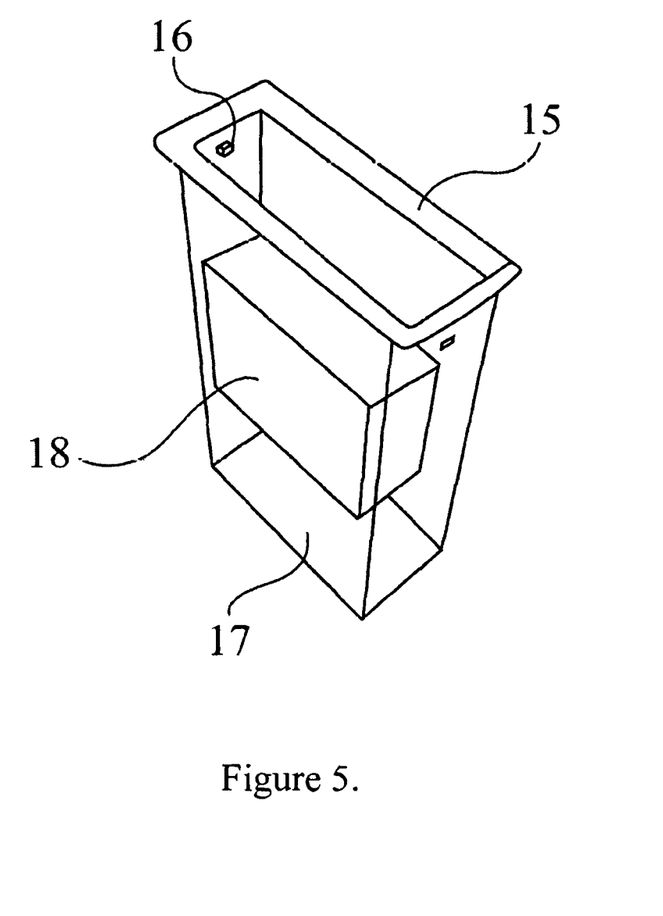
FIG. 5 is a perspective, transparent view of an alternative auxiliary cap with one chamber.
Figure 7:
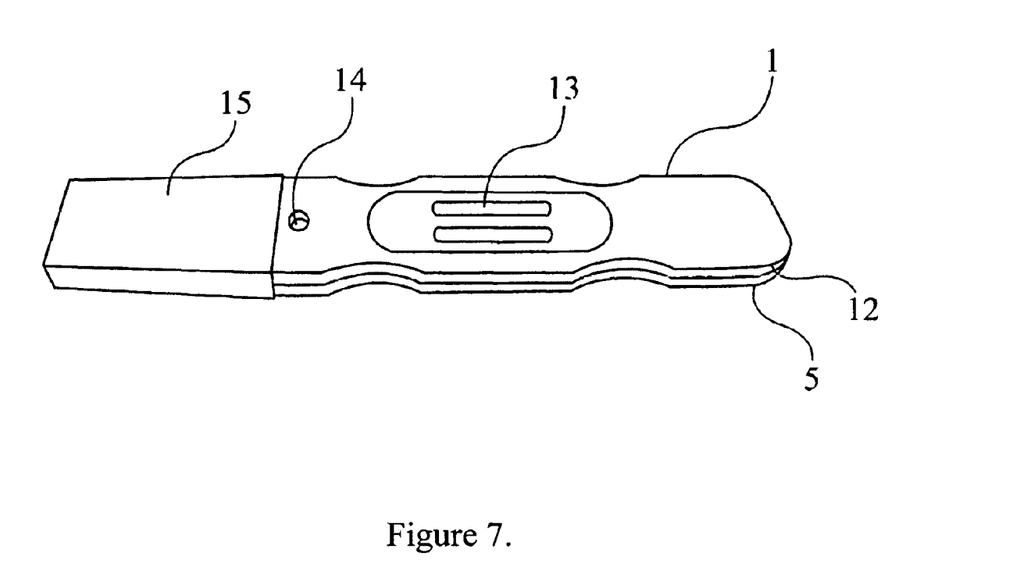
FIG. 7 is a perspective view of an analyte testing unit composed of two sample testing components placed into the liquid-holding chamber of a single chamber auxiliary cap.

FIG. 5 shows a transparent view of a single chamber auxiliary cap 15, which consists only of a liquid-holding chamber 17 containing the sponge or fibrous material 18 preloaded with the non-sample aqueous solution. FIG. 7 depicts the sample collecting tip 9 of the housing cassette locked into the liquid-holding chamber 17 of the single chamber auxiliary cap 15.

A small volume liquid or dry sample is collected by or added onto the sample collecting component 7 of the analyte testing unit 1. The sample of interest may or may not include target analytes. For liquid samples, the sample will travel up the sample collecting component 7, which will cause the colored marker 11 to also migrate up the sample collecting component 7 under capillary action and display in the sample sufficiency window 14 when a sufficient amount of sample has been added or collected to run the assay. The protective material 20 covering the top edge of the sample collecting component 7 will ensure that the colored marker 11 will remain on the sample collecting component 7 and will not migrate upwards along with the sample. For dry samples, the colored marker 11 will not indicate sample sufficiency. The sample sufficiency marker 11 and the protective material 20 are not required for the device to perform its intended function; thus, the device can also be produced and appropriately used without these features. After the colored marker 11 is signaled in the sample sufficiency window 14 for a liquid sample or after a dry sample has been added or collected, the sample collecting component 7 of the analyte testing unit 1 is placed into the liquid-holding chamber 17 of the auxiliary cap 15. The sample collecting tip 9 of the housing cassette will securely lock into the liquid-holding chamber 17 of the auxiliary cap 15 as shown in FIGS. 6 and 7, where the sample collecting component 7 will come into minimal contact with the preloaded sponge or fibrous material 18 in which at least 1 millimeter of the bottom of the sample collecting component 7 touches at least 0.05 millimeters of the sponge or fibrous material 18; and at least 10 millimeters of the top of the sample collecting component 7 does not contact the sponge or fibrous material 18. For dry samples, the front portion of the supplemental non-sample aqueous solution will dissolve the dry substance, causing the front flow to contain the heist concentration of the sample that will run through the binding area of the solid support 3 first. For liquid samples, the non-sample aqueous solution will push the sample by the capillary force so that the sample can run through the assay first, followed by the non-sample aqueous solution. The sponge or fibrous material 18 holds the non-sample aqueous solution in place, allowing the assay to be performed in various positions, such as vertically or horizontally. The sample will then migrate through the indicator holding area 4 wherein the visual indicator will selectively bind to the target analyte. Various analytes have a corresponding binding site to each type of indicator, and free analytes in the sample will form an analyte-indicator complex with the indicator as the sample migrates up the assay. The indicator will then flow along with the sample to the solid support 3. The sample first reaches the binding area, which contains an immobilized binder material that can specifically bind to the indicator, target analyte, or both. If the indicator is bound to free analytes in the sample, the analyte-indicator complex will not bind to the immobilized binder material because binding sites on the indicator material will be saturated by the analyte; thus, no visual indication will appear on the binding area of the solid support 3. If the indicator is not bound to free analytes in the sample, the indicator will bind to the immobilized binder material and display a visual indication on the binding area of the solid support 3. Visual indication in the binding area of the solid support 3 confirms the absence of the target analyte within a certain detection limit. Unbound indicator materials with then flow along with the sample to the validation area of the solid support 3, wherein a different immobilized ligand or binder material will bind the indicator and cause a visual indication to appear in the validation area. Visual indication in the validation area of the solid support 3 confirms that the indicator material properly flowed across the assay. The sample will then reach the sample ending area 2 of the test strip that will receive the remaining sample and indicator materials that have migrated through the solid support 3.

The indicator material is composed of a label linked to a ligand and can be visualized and/or measured based on color. The label consists of a visually identifiable or measureable agent, which can include but is not limited to a gold colloid, an enzyme, latex nanoparticles, iron nanoparticles, fluorescent material, and chemiluminescent material. The ligand of the label-ligand conjugate will selectively bind with the target analyte, immobilized binding material on the solid support 3, or both. For example, the analyte can be a molecule that acts as a target for an antibody. In this case, the ligands on the indicator will act as the antibody and the binding material immobilized on the solid support 3 will act similarly as the analyte to competitively bind the ligand. Based on the assay design, each analyte, ligand, and binding material can have distinct binding characteristics and specificities.

The device can be used with lateral flow immunoassay, lateral flow chemical assay, microfluidic immunoassay, or microfluidic chemical assay methods. The solid support 3 that provides the capillary flow is formed from microfluidic channels or absorbent material that is capable of transporting a liquid solution by capillarity, including but not limited to nitrocellulose, glass fiber, cellulose, and nylon. The selection of a suitable material is deemed to be within the scope of those skilled in the art of the teachings herein. The binder material on the solid support 3 can be directly immobilized or indirectly immobilized via conjugation to a large carrier molecule. The solid support 3 can contain more than one binding area and the indicator holding area can hold more than one indicator material, allowing an assay to detect multiple, distinguishable target analytes within a single sample.

The assayed sample can include but is not limited to solid, semi-solid, and liquid forms. The target analyte in the sample can include but is not limited to small molecule substances, large molecule substances, antibodies, antigens, enzymes, proteins, glycoproteins, peptides, drug molecules, small molecule chemicals, large molecule chemicals, nucleotides, DNA, RNA, lipids, and carbohydrates, as well as the metabolites of the above mentioned analytes.

Alternatively, the device can implement a technique other than competitive binding. For example, the analyte can be a large molecule that contains the same or different structures at different locations on the molecule. In this case, the ligands on the indicator will consist of a chemical material that can specifically bind to one of the structures on the analyte. The binding material immobilized on the solid support 3 can include another chemical material that can specifically bind to another structure on the analyte. This binding material can capture the analyte bound to the indicator, thereby resulting in a sandwich complex at the binding area of the solid support 3.

In order to successfully complete the assay with adequate results, a sufficient amount of sample is necessary. A sample volume as little as 15 microliters up to 500 microliters is considered a sufficient volume for this device.

This invention applies the techniques of a conventional lateral flow assay, but introduces the method and system for performing a rapid lateral flow assay with a dry or small volume liquid sample, thereby eliminating the need for sample dilution and large volume liquid samples to run an assay. This invention enables such dry and small volume liquid samples to be run on a lateral flow capillary assay as an undiluted or insignificantly diluted sample by strategic positioning and design of the sample collecting component 7 and the sponge or fibrous material 18 contained in the liquid-holding chamber 17 of the auxiliary cap 15, in addition to the capillary aid provided by the supplementary non-sample aqueous solution preloaded within the sponge or fibrous material 18. Thus, dry samples and small volume liquid samples do not need to be diluted to meet the larger sample volume requirements of a conventional, lateral flow assay and run to completion. The negligible or lack of sample dilution allows the assay to perform with maximum detectability, sensitivity, and accuracy as analytes within the sample are fundamentally preserved. The small liquid volume requirement of this device is particularly useful for cases in which a large volume of a liquid sample cannot be collected or is unavailable. For example, it can be very challenging for test administrators to collect large amounts of saliva from donors with dry mouth syndrome or sticky saliva, both of which are common oral fluid properties of drug users. In this case, the device will only require a small amount of saliva that is within an attainable range and can display a colored signal in the sample sufficiency window 14 to easily indicate when a sufficient amount of saliva has been collected. The minimization of the required sample volume to run a lateral flow assay and the indication of sample sufficiency enable the sample collection procedure for liquid samples to be completed more rapidly.

While this specification contains many specifics, these should not be construed as limitations on the scope of any invention or of what may be claimed, but rather as descriptions of features that may be specific to particular embodiments of the invention. It should be understood that various modifications can be made to the invention by one skilled in the art without departing from the scope of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Only a few implementations and examples are described and other implementations, enhancements and variations can be made based on what is described and illustrated in this specification.

The invention claimed is:

1. A system for performing lateral capillary flow assay, comprising:
   an analyte testing unit to test a presence of a target analyte(s) in a sample, wherein the analyte testing unit comprises:
      a sample collecting component composed of an absorbent material to collect the sample, comprising:
         a colored marker to indicate sample sufficiency
         a protective covering to prevent flow of the colored marker onto a sample receiving area of a sample testing component; and
      wherein the sample collecting component overlaps with the sample receiving area(s) of the sample testing component; and
      at least one sample testing component, each comprising:
         a sample receiving area composed of an absorbent material to receive the sample from the sample collecting component, and
         an indicator holding area to temporarily hold at least one type of indicator material that binds with a corresponding target analyte in the sample to form an analyte-indicator complex that flows across the sample testing component under capillary action, and
         at least one binding area on a solid support to immobilize at least one type of binder material configured to bind with the at least one type of indicator material, at least one analyte,
         or both the at least one analyte and at least one type of indicator material, wherein a presence of the corresponding type of indicator material at the at least one binding area indicates an absence of a corresponding type of target analyte, and
         a validation area on the solid support comprising a ligand or a binder material that selectively binds to the at least one type of indicator material to confirm that the at least one type of indicator material properly flowed across the sample testing component under capillary action; and
   a housing component that affixes the position of the sample collecting component and sample testing component, comprising:
      an area to expose the sample collecting portion of the sample collecting component, utilized for direct sample collection, and
      an area to display the binding area and validation area on the solid support of the sample testing component; and
      an area to display the colored marker on the sample collection component to indicate sufficient sample volume, and
   an auxiliary cap comprising:
      one liquid-holding chamber containing a flexible, sponge or fibrous material preloaded with a non-sample aqueous solution that will allow the sample to migrate across the analyte testing unit under capillary action when the sample collecting component is placed into the liquid-holding chamber, and
      a chamber to securely house the sample collection component and the corresponding housing area for the sample collection component, prior to sample collection.

2. The system of claim 1, wherein the sample collecting component will overlap with all sample receiving areas of all sample testing components used in the analyte testing unit.

3. The system of claim 1, wherein the sample collecting component is designed to collect dry sample or a minimum of 15 microliters of liquid sample.

4. The system of claim 1, wherein the colored marker that, when the minimum of 15 microliters of liquid sample is collected, will migrate downstream via capillary action to the location of the area of the housing component that displays the colored marker.

5. The system of claim 4, wherein the colored marker is composed of a colored or dye material that can be visualized based on color on the sample collecting component.

6. The system of claim 1, wherein the protective covering will wrap around the edge of the sample collecting component located downstream of the colored marker, and is designed to allow for direct contact between the sample collecting component and the sample receiving area.

7. The system of claim 1, wherein an airtight removable seal covers the opening of the liquid-holding chamber of the auxiliary cap.

8. The system of claim 1, wherein the engagement of the cap and the housing establishes physical contact and a continuous flow of liquid between the sponge or fibrous material of the liquid-holding chamber and the sample collecting component.

9. The system of claim 8, wherein the cap and the housing are designed so that the engagement of the two structures allows for at least the bottom 1 millimeter of the sample collecting component to press into the sponge or fibrous material in the liquid holding chamber, and allows for at least the top 5 millimeters of the sample component to avoid direct contact to the liquid in the liquid holding chamber.

\* \* \* \* \*